(12) United States Patent
Kane et al.

(10) Patent No.: US 6,985,776 B2
(45) Date of Patent: Jan. 10, 2006

(54) METHOD AND APPARATUS FOR CORONARY SINUS CANNULATION

(75) Inventors: Michael R. Kane, Higley, AZ (US); George K. Wong, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 185 days.

(21) Appl. No.: 10/423,113

(22) Filed: Apr. 25, 2003

(65) Prior Publication Data

US 2004/0215304 A1  Oct. 28, 2004

(51) Int. Cl.
*A61N 1/05* (2006.01)

(52) U.S. Cl. .................................. 607/122; 600/585
(58) Field of Classification Search ........ 607/116–128, 607/129; 606/129; 600/585
See application file for complete search history.

(56) References Cited

U.S. PATENT DOCUMENTS

| | | | |
|---|---|---|---|
| 3,674,014 A | 7/1972 | Tillander | |
| 4,928,688 A * | 5/1990 | Mower | 128/419 |
| 5,429,131 A | 7/1995 | Scheinman et al. | |
| 5,624,430 A * | 4/1997 | Eton et al. | 606/1 |
| 5,895,404 A * | 4/1999 | Ruiz | 606/185 |
| 6,015,414 A | 1/2000 | Werp et al. | |
| 6,126,647 A | 10/2000 | Posey et al. | |
| 6,212,419 B1 | 4/2001 | Blume et al. | |
| 6,836,687 B2 * | 12/2004 | Kelley et al. | 607/122 |

* cited by examiner

*Primary Examiner*—George R. Evanisko
*Assistant Examiner*—Alyssa M. Alter
(74) *Attorney, Agent, or Firm*—Michael C. Soldner and Girma Wolde-Michael

(57) ABSTRACT

A system and method of positioning an implantable medical device lead within a patient that includes introducing a distal tip of a first elongated member along a first location within the patient through a first introducing path, and introducing a distal tip of a second elongated member within the first location through a second introducing path. The distal tip of the first elongated member is engaged with the distal tip of the second elongated member at the first location, and, upon engagement, the distal tip of the first elongated member is advanced to a second location via the second elongated member as the second elongation member is advanced to the second location.

10 Claims, 13 Drawing Sheets

US 6,985,776 B2

METHOD AND APPARATUS FOR CORONARY SINUS CANNULATION

TECHNICAL FIELD

The invention relates to placement of cardiac leads, and more particularly to cannulation of the coronary sinus for lead placement.

BACKGROUND

In the medical field, implantable leads are used with a wide variety of medical devices. For example, implantable leads are commonly used to form part of implantable cardiac pacemakers that provide therapeutic stimulation to the heart by delivering pacing, cardioversion or defibrillation pulses. The pulses can be delivered to the heart via electrodes disposed on the leads, e.g., typically near distal ends of the leads. In that case, the leads position the electrodes with respect to various cardiac locations so that the pacemaker can deliver pulses to the appropriate locations. Leads are also used for sensing purposes, or both sensing and stimulation purposes.

A number of challenges exist with respect to medical leads. In particular, new and improved lead designs are often needed to facilitate medical implantation to specific locations within a patient. For example, as more advanced and complex pacing techniques are developed, it becomes desirable to facilitate lead implantation at new cardiac locations. Some recent advancements in pacing have made use of non-conventional locations for delivery of pacing pulses, such as left ventricular locations, atrial roof locations and epicardium locations.

Cannulation, or lead placement, of the coronary sinus is a necessary part of the surgery that implements an IMD into the human body. A lead is placed in the great vein proximate the left ventricle to aid in the synchronous pumping of the ventricles. Placement of the lead in the great vein can be very difficult because of navigation issues resulting from undesirable angles and lack of lead maneuverability. Coronary sinus cannulation is a substantial barrier to predictably efficient implantation of coronary sinus lead.

SUMMARY

In general, the invention is directed to techniques for coronary sinus cannulation. Cannulation of the coronary sinus enables placement of cardiac leads in the great vein proximate the left ventricle. The cardiac leads carry sensing electrodes, stimulation electrodes or both. The techniques described herein involve introduction of a first and second elongated member into the right atrium of the human heart. One of the elongated members serves to aid in the positioning of the other elongated member within the coronary sinus to support lead placement.

The first elongated member may take the form of a steerable catheter that is introduced into the right atrium via the femoral vein and inferior vena cava. The second elongated member may take the form of a guidewire that is introduced into the right atrium via the superior vena cava. The distal tip of the guidewire engages the distal tip of the catheter when the catheter and guidewire are introduced into the right atrium.

The techniques may further involve guiding the steerable catheter into the coronary sinus. In turn, the guidewire travels into the coronary sinus with the catheter, permitting introduction of a sheath over the guidewire to cannulate the coronary sinus. Upon deployment of the sheath, the guidewire is withdrawn and a cardiac lead is inserted in its place.

Ultimately, the sheath is withdrawn, leaving the cardiac lead positioned within the coronary sinus and, more particularly, the great vein proximate the left ventricle. In some embodiments, the guidewire and catheter rely on magnetic engagement. In particular, one or both of the guidewire and catheter carry a magnet to promote engagement by magnetic attraction. The magnet may be a permanent magnet or an electromagnet.

In one embodiment, the invention is directed to a method that includes introducing a distal tip of a first elongated member into the right atrium of a human heart via the femoral vein and the inferior vena cava, introducing a distal tip of a second elongated member into the right atrium of the heart via the superior vena cava, engaging the distal tip of the first elongated member with the distal tip of the second elongated member, and guiding the second elongated member into the coronary sinus, wherein the distal tip of the first elongated member travels into the coronary sinus with the distal tip of the second elongated member.

In another embodiment, the invention is directed to a system that includes a first elongated member sized for introduction into the right atrium of a human heart via the femoral vein and the inferior vena cava, the first elongated member including a first engagement structure proximate a distal end of the first elongated member, and a second elongated member sized for introduction into the right atrium of the heart via the superior vena cava, the second elongated member including a second engagement structure proximate a distal end of the second elongated member for engagement with the first engagement structure of the first elongated member upon introduction of the distal ends of the first and second elongated members into the right atrium.

In an added embodiment, the invention is directed to a catheter sized for introduction into the right atrium of the heart via the femoral vein and the inferior vena cava, the catheter including an engagement structure proximate a distal end of the catheter for engagement with a guidewire upon introduction of distal ends of the catheter and the guidewire into the right atrium.

In a further embodiment, the invention is directed to a guidewire sized for introduction into the right atrium of a human heart via the superior vena cava, the guidewire including a first engagement structure proximate a distal end of the guidewire for engagement with a catheter upon introduction of distal ends of the catheter and the guidewire into the right atrium.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
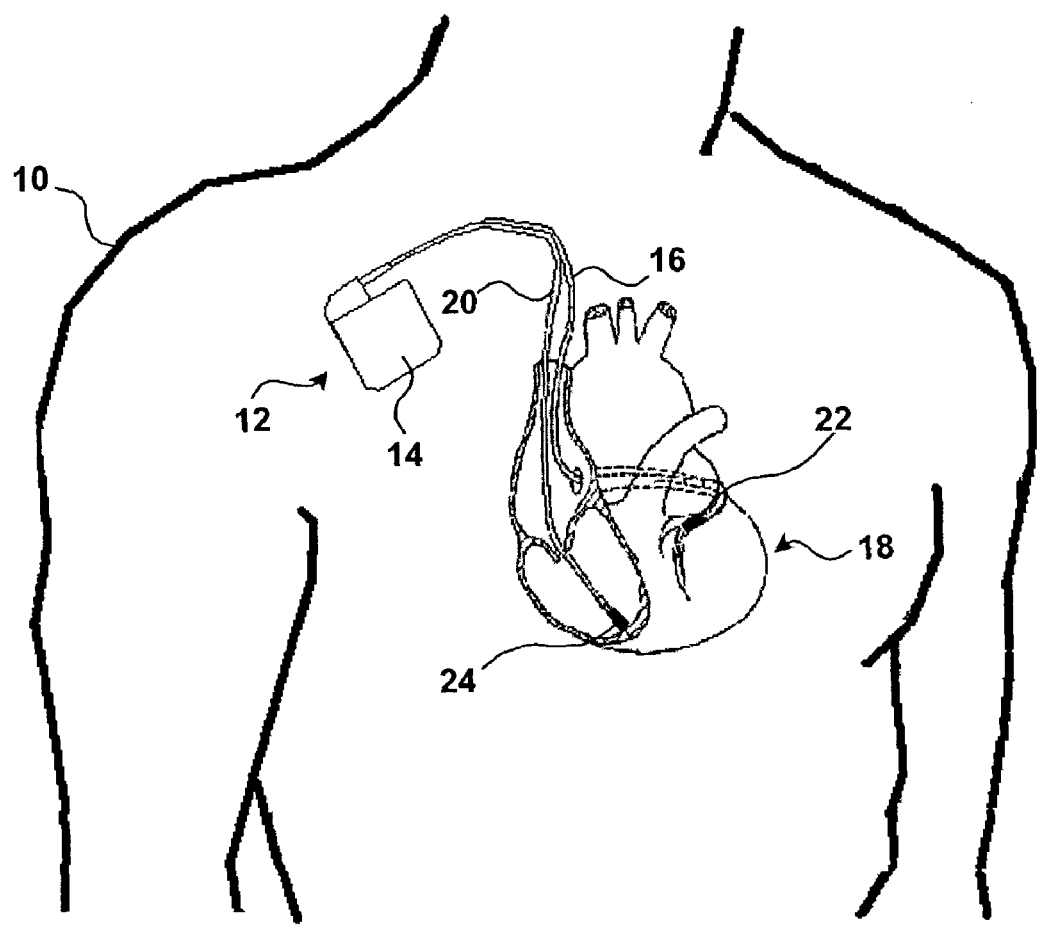
FIG. 1 is a schematic view of an implantable medical device (IMD) implanted within a human.

FIG. 1 is a schematic diagram illustrating an implantable medical device (IMD) 12 within the body of a patient 10. Although IMD 12 is shown as being located in the right pectoral region, it may be located in the left pectoral region, the abdomen or other areas within the body patient 10. In the example of FIG. 1, IMD 12 includes a lead deployed for contact with the left ventricle via the coronary sinus and the great vein. In accordance with the invention, deployment of the left ventricular lead is accomplished by a technique for coronary sinus cannulation, as described herein. IMD 12 represents one embodiment that may benefit from coronary sinus cannulation techniques according to the invention.

As shown in FIG. 1, IMD 12 includes an IMD housing 14 containing an implanted pulse generator, and one or more cardiac leads 16 and 20 coupled to IMD housing 14. Leads 16, 20 each position one or more electrodes 22, 24 with respect to heart 18. Electrodes 22, 24 sense electrical signals attendant to the depolarization and repolarization of heart 18, and deliver pacing pulses generated by pacemaker device 14 for causing depolarization of cardiac tissue in the vicinity of the respective electrode 22, 24. Electrodes 22, 24 may include unipolar or bipolar electrodes, as are well known in the art. Although FIG. 1 illustrates leads positioned in the ventricles, it is understood that the invention may be practiced in pacemaker systems having any number of leads, including a lead positioned within the right atrium.

Implantable leads 16, 20 may include any number of additional electrodes (not shown) distributed along the length of the respective lead. Electrodes 22, 24 or other electrodes may be used for sensing and/or delivery of stimulation pulses. Additional electrodes (not shown) may also be used for delivery of high voltage defibrillation or cardioversion shocks.

Electrodes 22, 24 can be made from an electrically conductive, biocompatible material such as elgiloy, platinum, platinum-iridium, platinum-iridium oxide, sintered platinum powder or other residue product after combustion with some high heat source, platinum coated with titanium-nitride, pyrolytic carbon, or the like. Electrodes 22, 24 are electrically coupled to one or more conductive filars that extend along the body of the respective lead 16, 20, e.g., in a coiled construction.

In some embodiments, electrodes 22, 24 form a substantially cylindrical ring of conductive material that extends about an exterior wall of leads 16, 20. For example, electrodes 22, 24 may extend the entire 360 degrees about leads 16, 20, or to some lesser extent. In some embodiments, leads 16, 20 may be tubular but not necessarily cylindrical. For example, electrodes 22, 24 and leads 16, 20 may have alternative cross sections, e.g., square, rectangular, hexagonal, oval, or the like. In any case, electrodes 22, 24 are coupled to one or more electrically conductive filars that extend along the length of leads 16, 20. The filars are typically coiled to define a lumen of the respective lead 16, 20.

Additionally, FIG. 1 illustrates deployment of cardiac lead 16 through the superior vena cava, through the right atrium, and into the coronary sinus where it is positioned for sensing, stimulation, or both. As mentioned above, deployment and placement of cardiac lead 16 in the coronary sinus takes advantage of coronary sinus cannulation techniques in accordance with the invention. In general, a technique for coronary sinus cannulation in accordance with the invention involves introduction of a first and second elongated member into the right atrium of the human heart. One of the elongated members serves to aid in the positioning of the other elongated member within the coronary sinus to support lead placement.

The first elongated member may take the form of a steerable catheter that is introduced into the right atrium via the femoral vein and inferior vena cava. The second elongated member may take the form of a guidewire that is introduced into the right atrium via the superior vena cava. The distal tip of the guidewire engages the distal tip of the catheter when the catheter and guidewire are introduced into the right atrium.

The coronary sinus cannulation technique further involves guiding the steerable catheter into the coronary sinus. In turn, the guidewire travels into the coronary sinus with the catheter, permitting introduction of a sheath over the guidewire to cannulate the coronary sinus. Upon deployment of the sheath, the guidewire is withdrawn and a cardiac lead is inserted in its place.

Ultimately, the sheath is withdrawn, leaving the cardiac lead positioned within the coronary sinus and, more particularly, the great vein proximate the left ventricle. In some embodiments, the guidewire and catheter rely on magnetic engagement. In particular, one or both of the guidewire and catheter may carry a magnet to promote engagement by magnetic attraction. The magnet may be a permanent magnet or an electromagnet.

Figure 2:
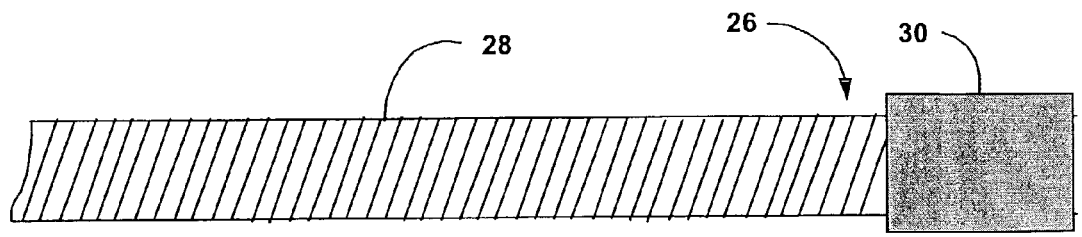
FIG. 2 is a schematic diagram illustrating a first elongated member that includes a guidewire and an engagement structure.

FIG. 2 is a schematic diagram illustrating a first elongated member 26 for use in a technique for coronary sinus cannulation in accordance with the invention. First elongated member 26 may be a steerable catheter 28 having an engagement structure 30. Engagement structure 30 is attached proximate the distal tip of catheter 28. In one embodiment, engagement structure 36 includes a magnet to support magnetic engagement with another elongated member as will be described. The magnet may be a permanent magnet or an electromagnet that is selectively energized to initiate the magnetic engagement.

In another embodiment, the distal tip of elongated member 26 is made of a material that is attracted by a magnet that is part of a second elongated member. In other embodiments, the sinus cannulation technique relies on magnets carried by both elongated members. The catheter may enter the body of patient 10 through the femoral vein and travel to the coronary sinus via the inferior vena cava and the right atrium.

Figure 3:
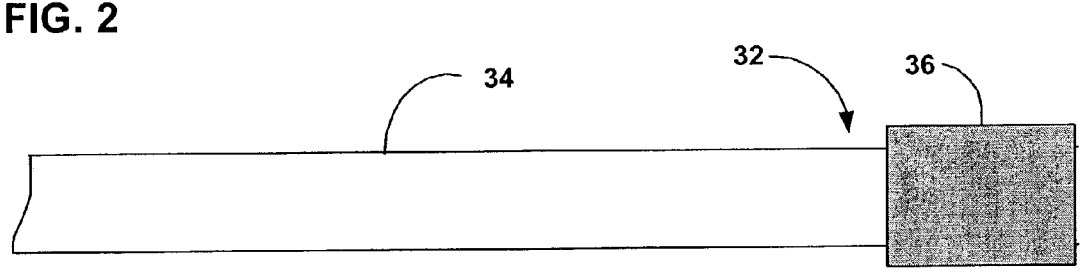
FIG. 3 is a schematic diagram illustrating a second elongated member that includes a steerable catheter and an engagement structure.

FIG. 3 is a schematic diagram illustrating a second elongated member 32 for use in a technique for coronary sinus cannulation in accordance with the invention. Second elongated member 32 may be a guidewire 34 and includes an engagement structure 36. Engagement structure 36 is attached to the distal tip of guidewire 34. In one embodiment, engagement structure 36 is a magnet to support a magnetic engagement. The magnet may be a permanent magnet or an electromagnet, which may be energized to initiate the magnetic engagement.

In another embodiment, the distal tip of elongated member 32 is made of a material that is attracted by a magnet that is part of elongated member 26. Guidewire 34 enters the body of patient 10 and travels to the coronary sinus via the superior vena cava and the right atrium. Thus, in some embodiments, the distal ends of first and second elongated members 26, 32 each include magnets to promote engagement between the distal ends of the elongated members. As discussed above, the magnets may be permanent magnets that are poled for attraction to one another.

Alternatively, the magnets may be electromagnets that are energized via electrical conductors that travel along the lengths of the respective elongated members 26, 32. As further alternatives, structural engagement members such as hook and loop arrangements, keyed structures, and the like may be employed to permit mechanical engagement of the distal tips of elongated members 26, 32. In each case, it is desirable to engage the distal tips of elongated members 26, 32, but also to selectively disengage the elongated members.

Figure 4:
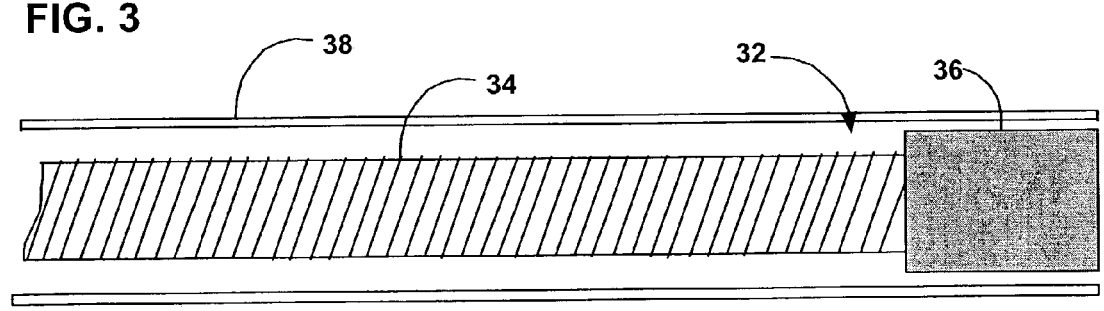
FIG. 4 is a schematic diagram illustrating a sheath advancing over a guidewire as shown in FIG. 2.

FIG. 4 is a schematic diagram illustrating an introduction sheath 38 advanced over second elongated member 32 during the course of a coronary sinus cannulation procedure in accordance with the invention. Introduction sheath 38 is a hollow-core structure that fits over second elongated member 32 for travel into the coronary sinus via the superior vena cava and the right atrium. Thus, second elongated member 32, e.g., a guidewire, serves as a guide for introduction of sheath 38 into the coronary sinus. As will be described, second elongated member 32 is withdrawn from sheath 38, providing space for another structure to pass through it. In particular, once second elongated member 32 is withdrawn from sheath 38 and heart 18, a cardiac lead is introduced through sheath 38 for travel into the coronary sinus.

Figure 5:
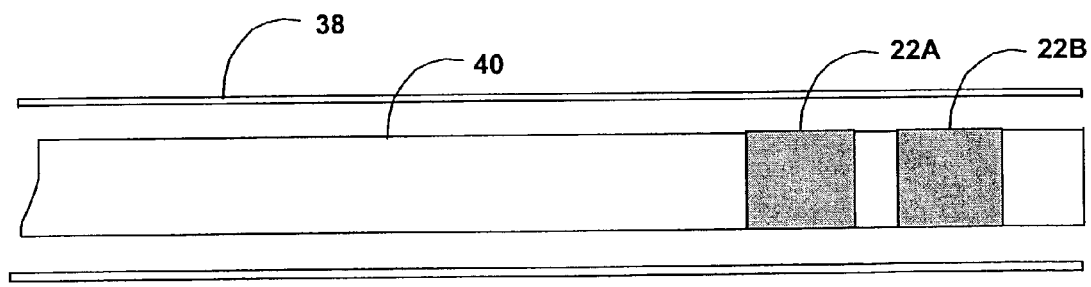
FIG. 5 is a schematic diagram illustrating a cardiac lead advanced through the sheath.

FIG. 5 is a schematic diagram illustrating a cardiac lead 40 advanced through sheath 38. Cardiac lead 40 carries a sensing electrode, a stimulation electrode or both. The diagram shows two electrodes, 22A and 22B, carried by the cardiac lead. Sheath 38 acts as a guide for cardiac lead 40. Cardiac lead 40 enters the heart through the superior vena cava via a proximal port of sheath 38 and continues through the right atrium and into the coronary sinus.

Figure 6:
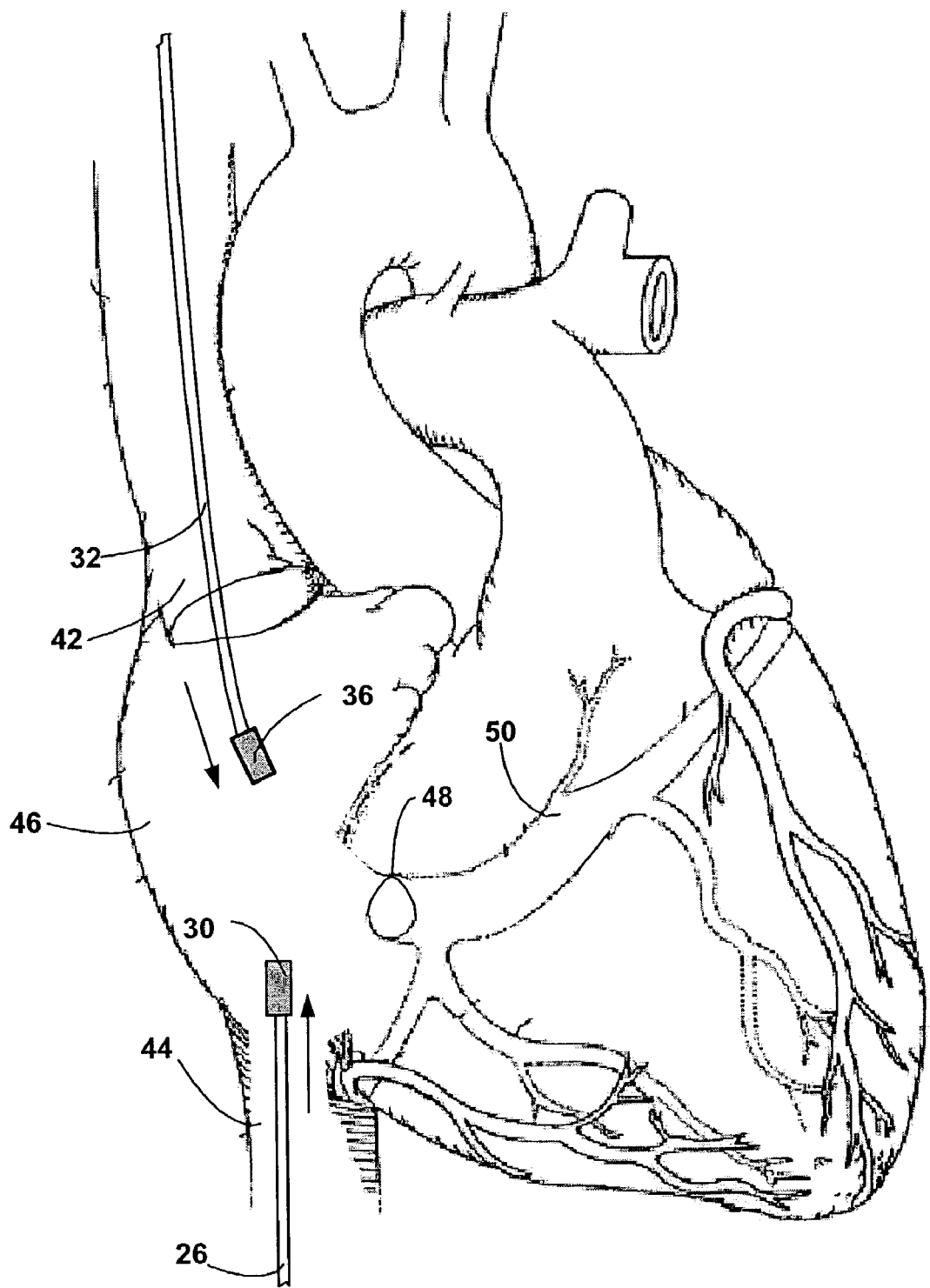
FIG. 6 is a schematic diagram illustrating the introduction of the first elongated member and the second elongated member into the right atrium.

FIG. 6 is a schematic diagram illustrating the introduction of first elongated member 26 and second elongated member 32 into the right atrium 46. First elongated member 26 enters into right atrium 46 via the femoral vein and the inferior vena cava 44, and may take the form of a steerable catheter as described with reference to FIG. 2. Second elongated member 32 enter into right atrium 46 via superior vena cava 42. In one embodiment, second elongated member 32 is a guidewire 34 as described with reference to FIG. 3.

Figure 7:
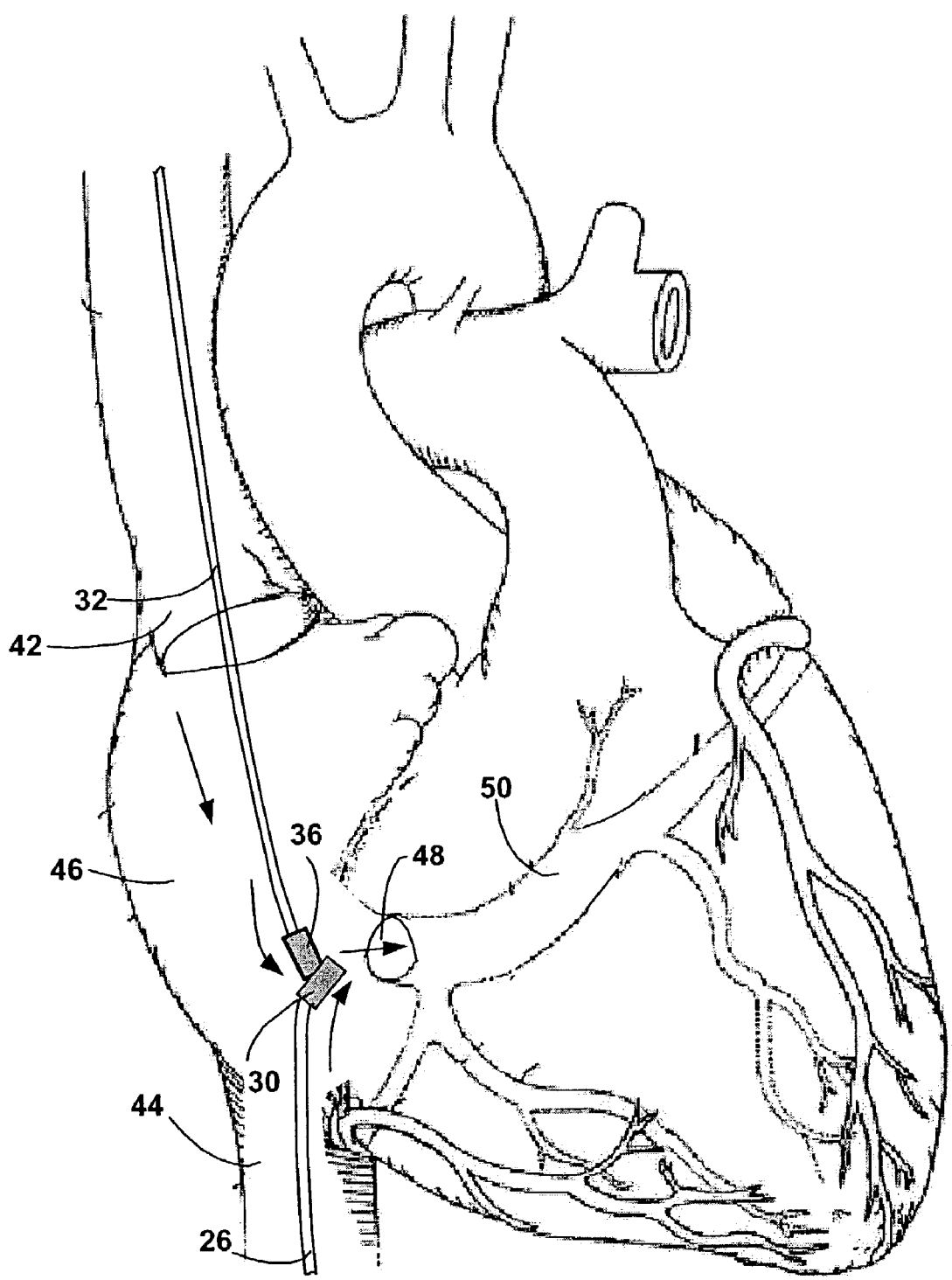
FIG. 7 is a schematic diagram illustrating the engagement of the first and second elongated members in the right atrium.

FIG. 7 is a schematic diagram illustrating the distal tips of first elongated member 26 and second elongated member 32 engaged in the right atrium. The engagement of the distal tip of the first elongated member 26 with the distal tip of the second elongated member 32 may involve magnetic engagement of the distal tips. In particular, the distal tip of at least one of the first and second elongated members 26, 32 includes a magnet to support magnetic engagement. In some embodiments, the magnet is an electromagnet, which is energized to initiate the magnetic engagement.

FIG. 7 shows the distal tip of first elongated member 26 including engagement structure 30. In one embodiment, the distal tip of elongated member 32 is made of a material that is attracted by a magnet that is part of elongated member 26. In another embodiment, the distal tip of elongated member 26 is made of a material that is attracted by a magnet that is part of elongated member 32. In other embodiments, both elongated members 26, 32 carry magnets, e.g., permanent magnets or electromagnets.

First elongated member 26 is a steerable catheter 28 that permits facile positioning and guidance relative to coronary sinus. Second elongated member 32 includes a guidewire 34. In general, upon engagement, steerable catheter 28 serves to steer guidewire 34 toward coronary sinus 48 and into the great vein 50. In this manner, guidewire 34 is deployed within great vein 50 to aid in deployment of sheath 38 and, ultimately, cardiac lead 40. Consequently, the distal tip of cardiac lead 40 can be deployed in contact with the left ventricle, and the proximal tip of the cardiac lead thereafter coupled to IMD 10 (FIG. 1).

Figure 8:
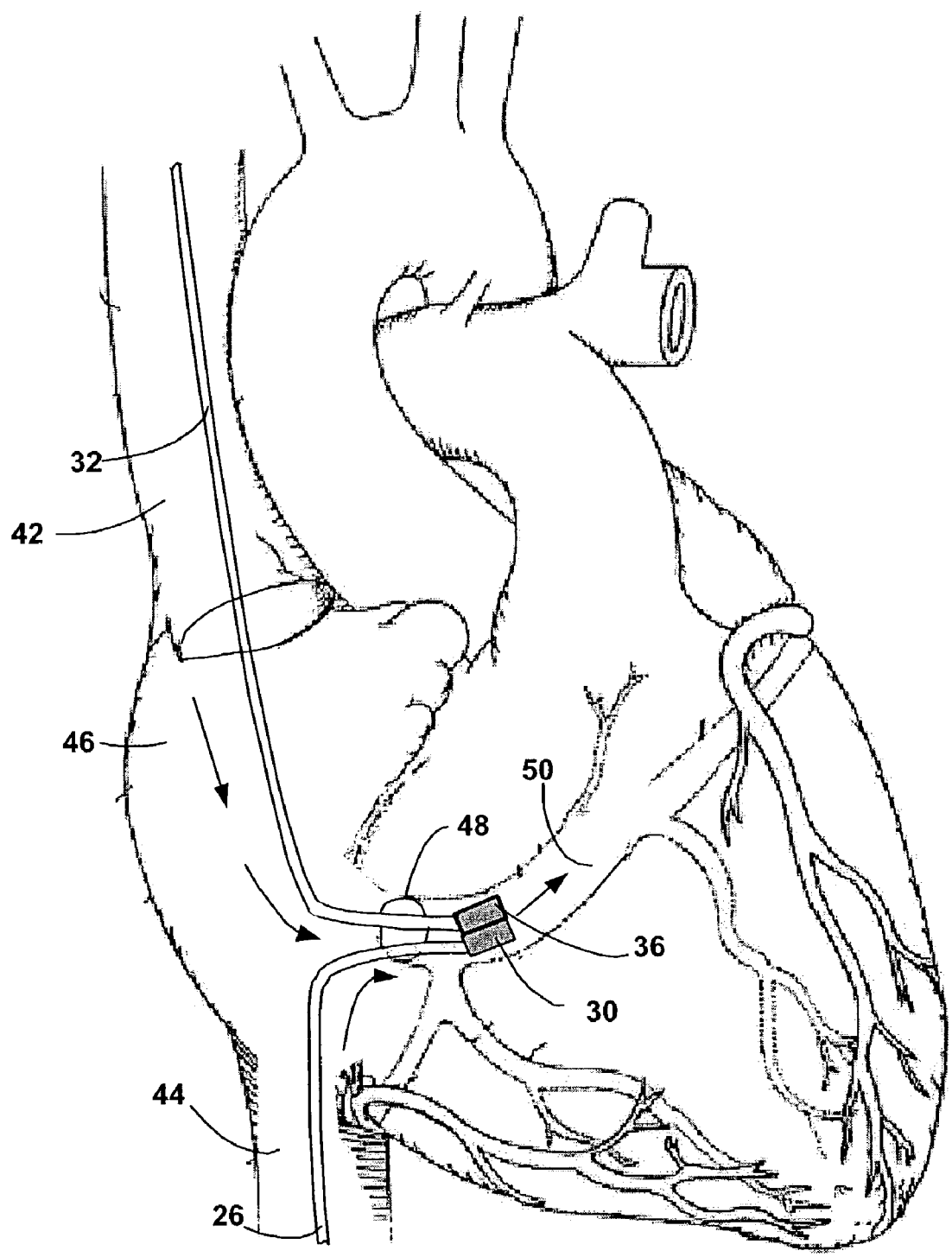
FIG. 8 is a schematic diagram illustrating the first elongated member traveling with the second elongated member into the coronary sinus.

FIG. 8 is a schematic diagram illustrating introduction of first elongated member 26 and second elongated member 32 into coronary sinus 48. In particular, engagement structure 30 of first elongated member 26 travels into coronary sinus 50 with engagement structure 36 of second elongated member 32 after the distal tip of first elongated member 26 is fixedly engaged with the distal tip of elongated member 32 via engagement structure 30 and 36, respectively, in the right atrium. In this example, the maneuverability of first elongated member 26, e.g., a steerable catheter, serves to assist in pulling second elongated member 32, e.g., a guidewire, into coronary sinus 48. In other words, one of the elongated members 26, 32 serves to aid in the positioning of the other elongated member within coronary sinus 50 to support lead placement.

Figure 9:
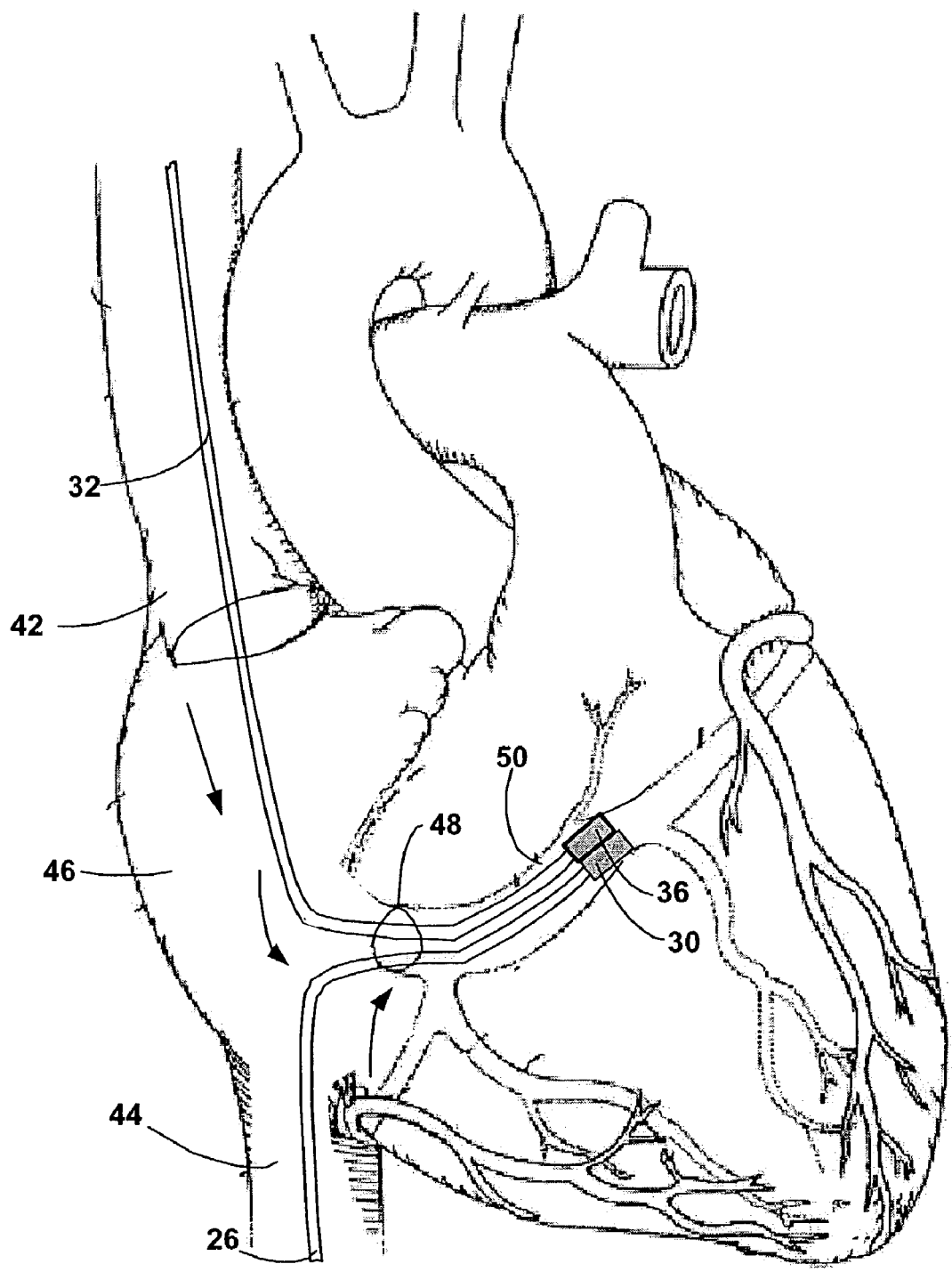
FIG. 9 is a schematic diagram illustrating the first and second elongated members residing within the coronary sinus.

FIG. 9 is a schematic diagram illustrating travel of first and second elongated members 26, 32 into great vein 50 via coronary sinus 48. First elongated member 26 and elongated member 32 maintain engagement with one another as they continue to travel into great vein 50.

Figure 10:
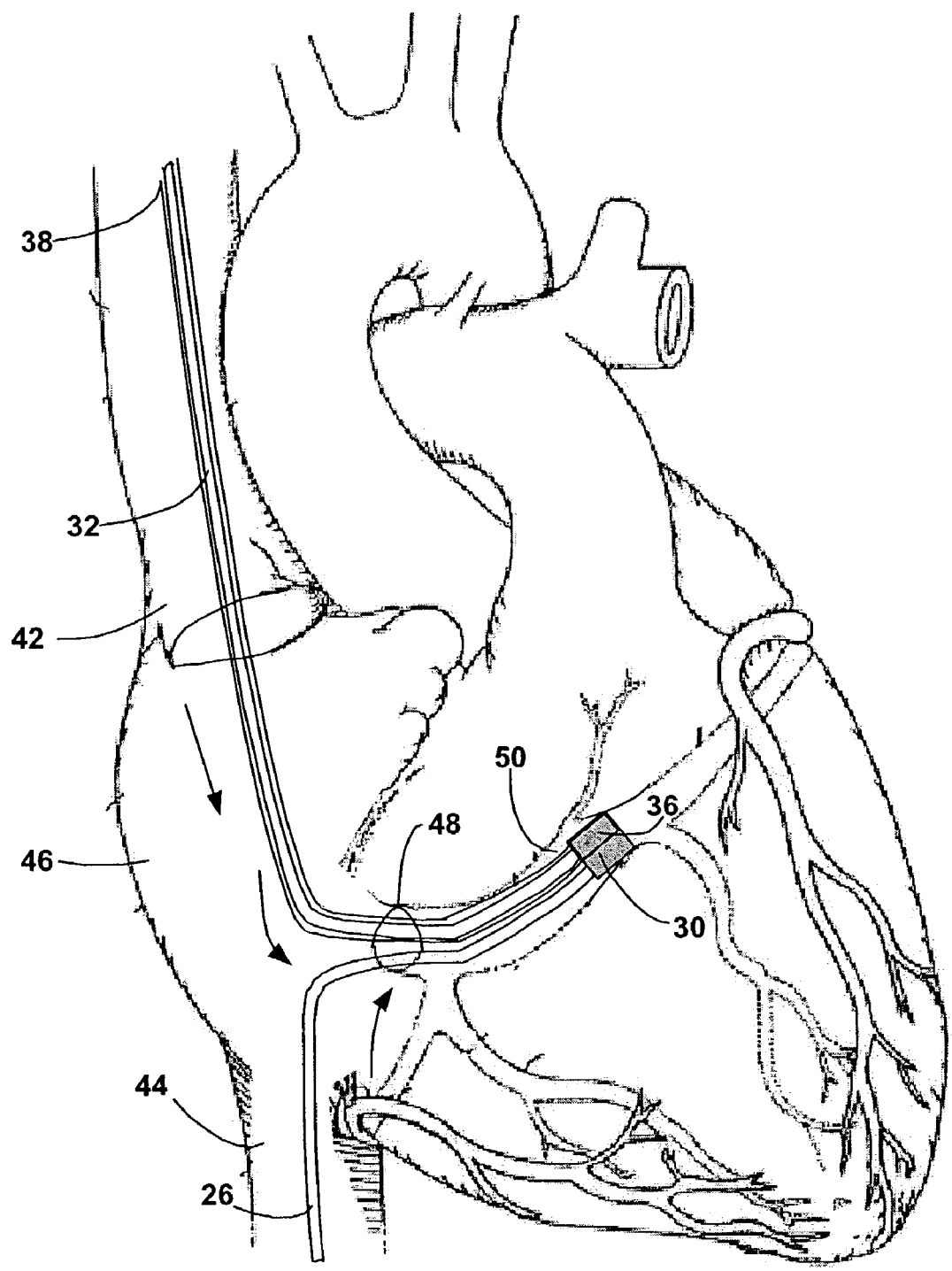
FIG. 10 is a schematic diagram illustrating a sheath advanced over the second elongated member.

FIG. 10 is a schematic diagram illustrating introduction of sheath 38 second elongated member 32. First elongated member 26 maintains the engagement with elongated member 32 until sheath 38 advances over elongated member 32 into coronary sinus 50. Once sheath 38 is advanced over elongated member 32 into the coronary sinus, elongated member 32 may be disengaged from elongated member 26 by assertion of the sheath.

In particular, sheath 38 disengages the coupling between elongated member 26 and elongated member 32 simply by pushing the members apart with force. In an embodiment in which the engagement between elongated members 26, 32 is magnetic, an electromagnet carried by one or both of the elongated members may be deenergized to terminate the magnetic engagement. Once the engagement is terminated, elongated member 26 and elongated member 32 both may be withdrawn from the heart.

Figure 11:
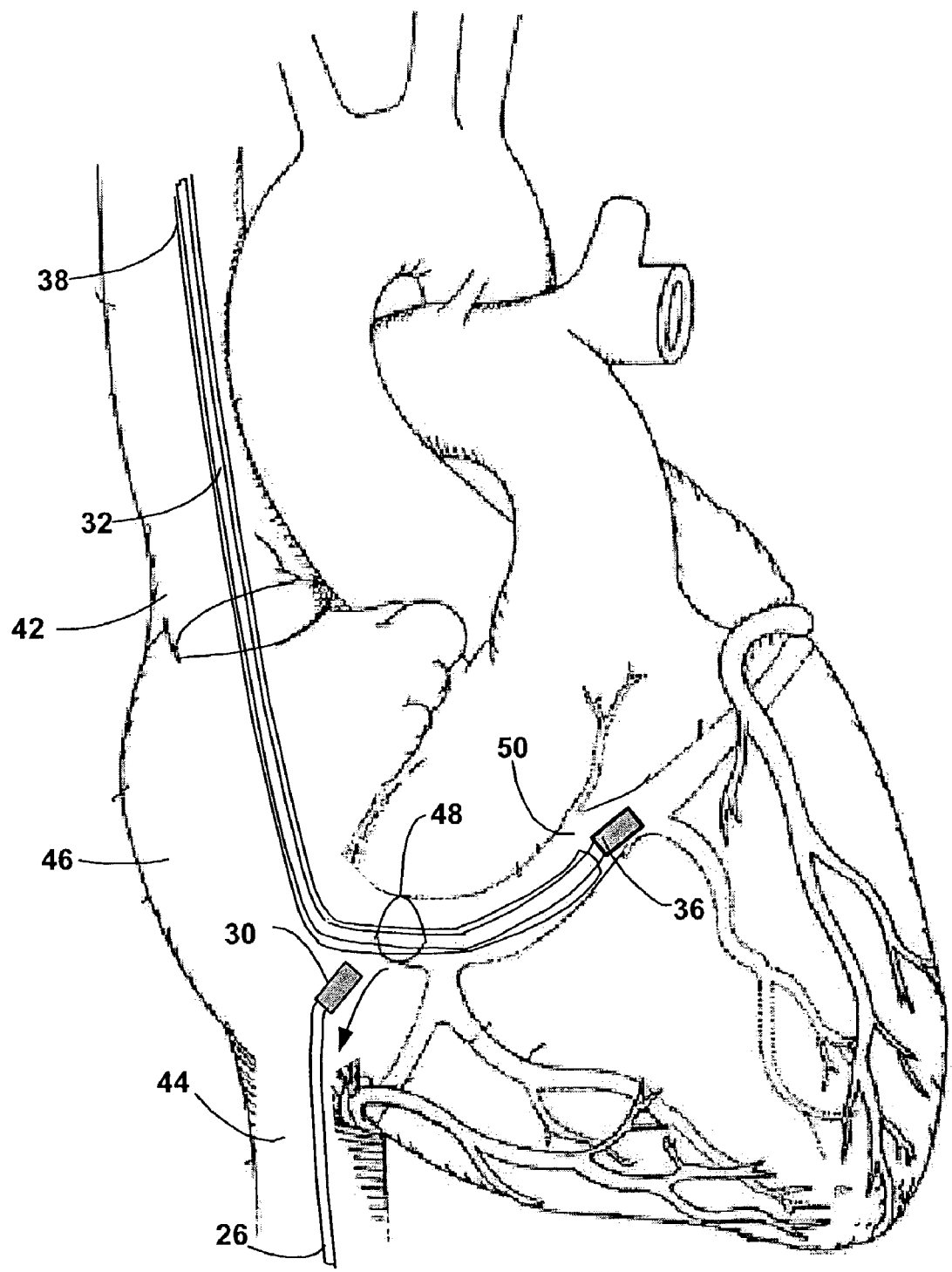
FIG. 11 is a schematic diagram illustrating withdrawal of the first elongated member from the heart.

FIG. 11 is a schematic diagram illustrating disengagement of first elongated member 26 from second elongated member 32, and withdrawal of first elongated member 26 from the heart via coronary sinus 50, right atrium 46, and inferior vena cava 44. Elongated member 32 also is withdrawn from the heart, leaving sheath 38 placed in coronary sinus 48 and great vein 50.

Figure 12:
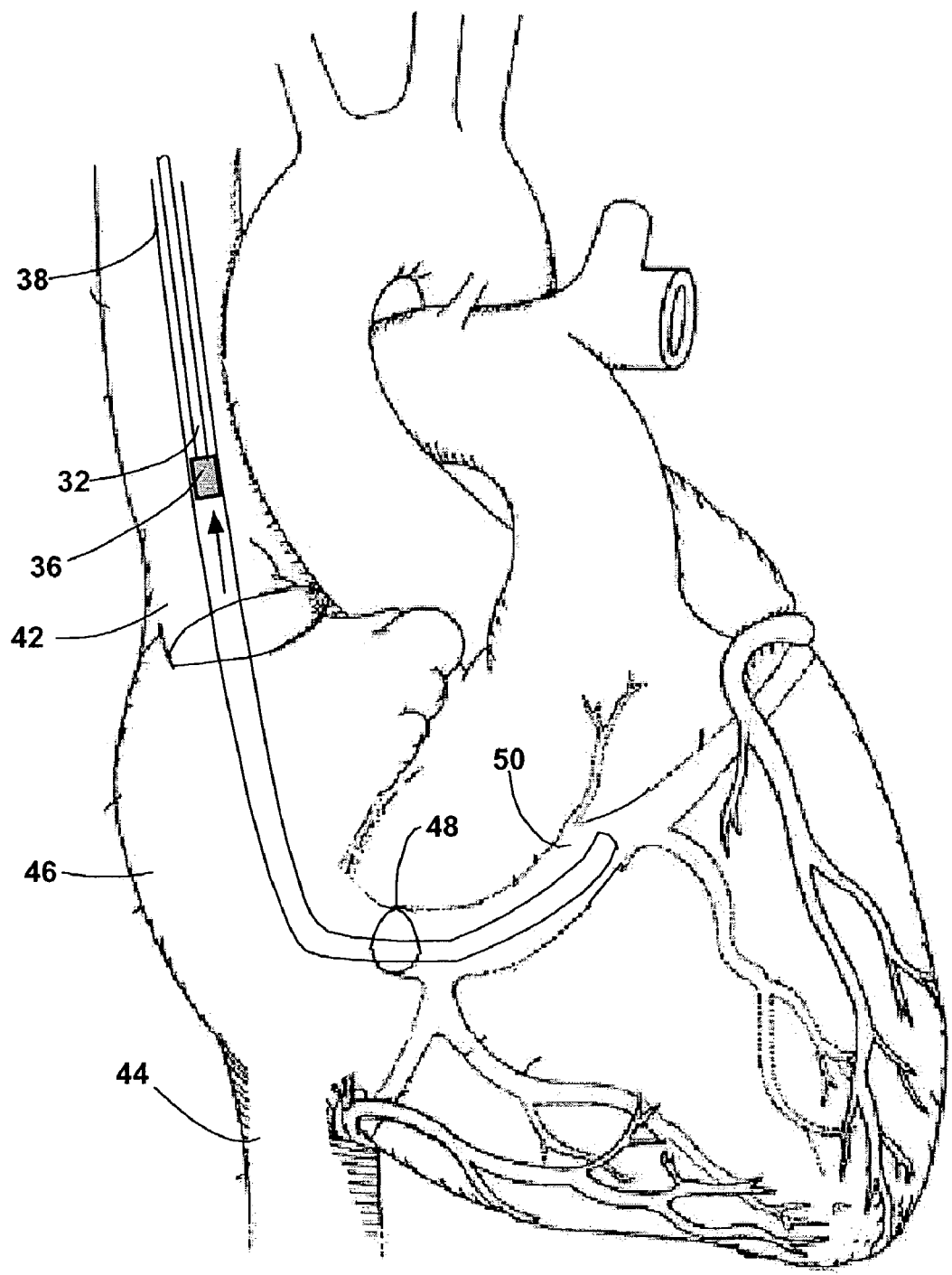
FIG. 12 is a schematic diagram illustrating the sheath residing in the coronary sinus, and introduction of a cardiac lead via the sheath.

FIG. 12 is a schematic diagram illustrating sheath 38 residing in great vein 50. In FIG. 12, second elongated member 32 is withdrawn from the heart via coronary sinus 50, right atrium 46, and superior vena cava 42. Withdrawal of second elongated member 32 leaves sheath 38 available to guide cardiac lead 40 to great vein 50.

Figure 13:
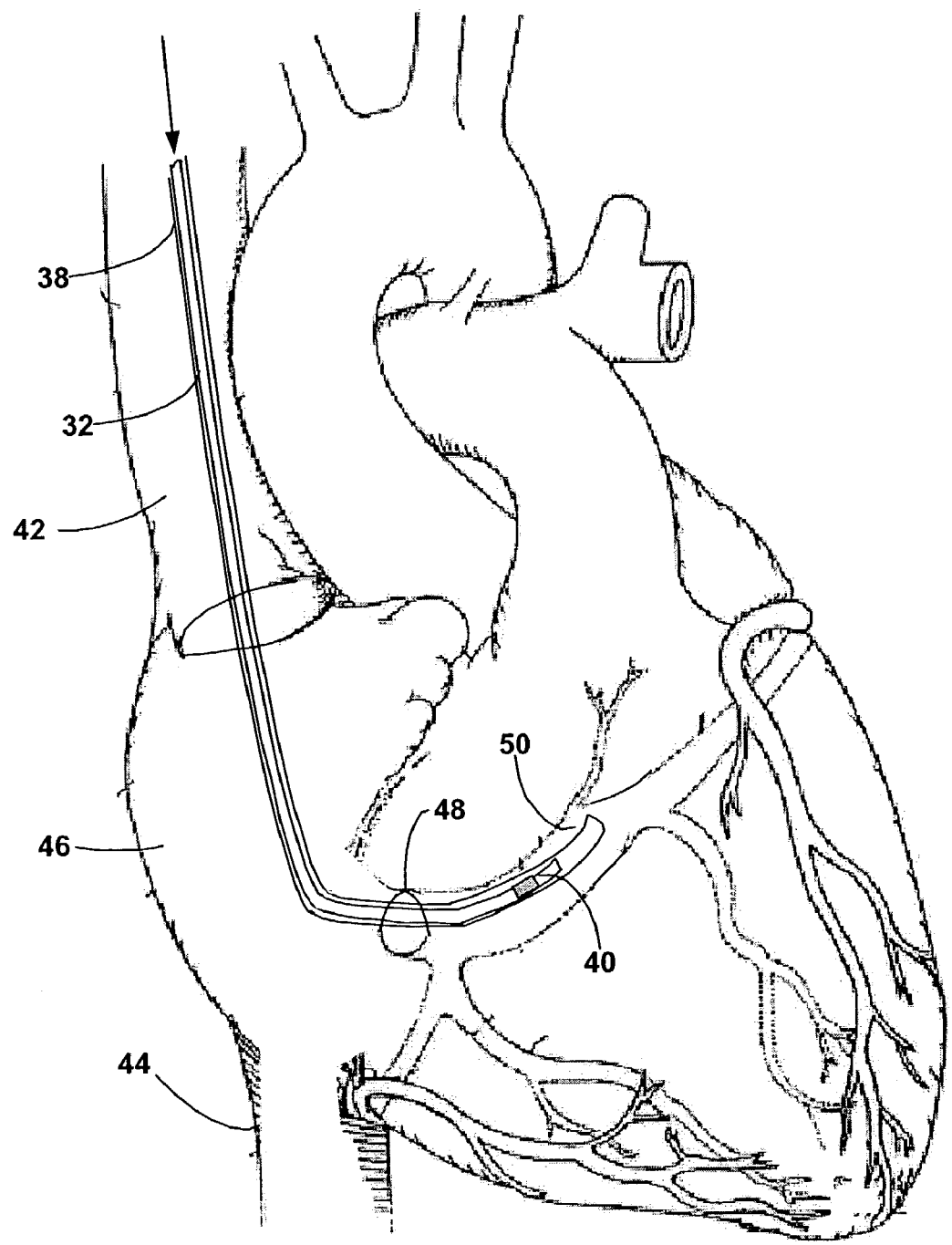
FIG. 13 is a schematic diagram illustrating introduction of the cardiac lead into the coronary sinus via the sheath.

FIG. 13 is a schematic diagram illustrating introduction of cardiac lead 40 through sheath 38 and into great vein 50. As shown in FIG. 13, sheath 38 provides a ready guide for advancement of cardiac lead 40 to a desired position.

Figure 14:
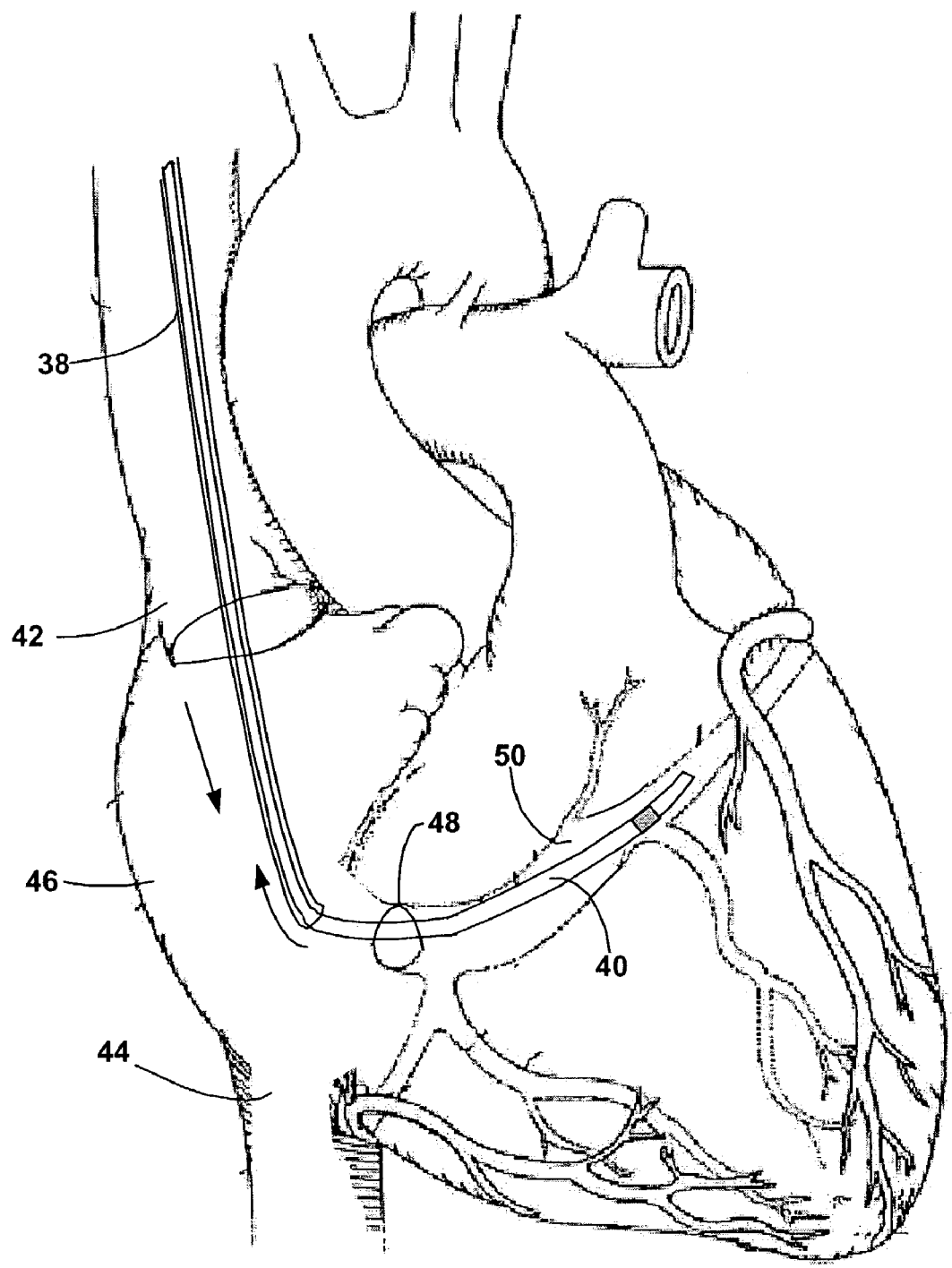
FIG. 14 is a schematic diagram illustrating withdrawal of the sheath from the heart.

FIG. 14 is a schematic diagram illustrating cardiac lead 40 residing in great vein 50 as sheath 38 is withdrawn from the heart via coronary sinus 48, right atrium 46, and superior vena cava 42. One sheath 38 is withdrawn, only cardiac lead 40 remains within great vein 50. The proximal end of cardiac lead 40 then can be connected to a connector block associated with IMD 10.

Figure 15:
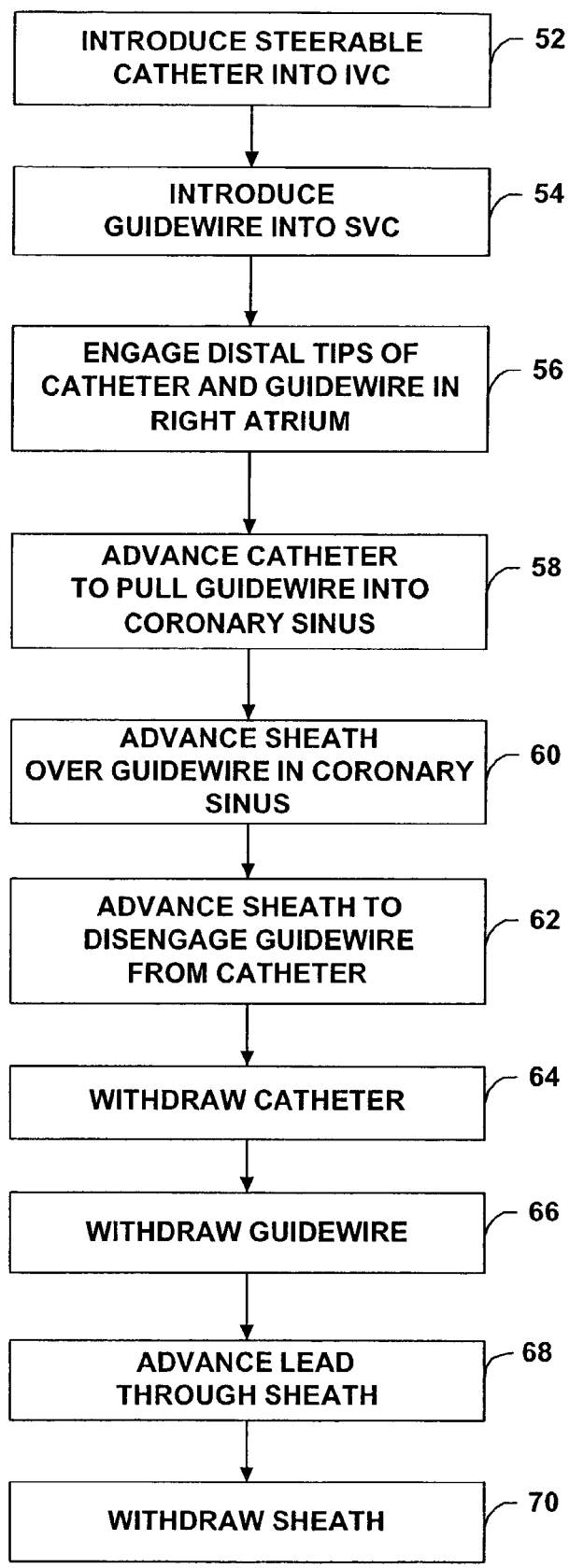
FIG. 15 is a flow diagram illustrating an coronary sinus cannulation in accordance with the invention.

FIG. 15 is a flow diagram illustrating coronary sinus cannulation in accordance with the invention. Cannulation of the coronary sinus 50 enables placement of cardiac lead 40 in great vein 50 proximate the left ventricle. Cardiac lead 40 may carry sensing electrodes, stimulation electrodes or both. As shown in FIG. 15, a method for coronary sinus cannulation involves introducing a steerable catheter into inferior vena cava 44 (52). Next, a guidewire is introduced into superior vena cava 42 (54). Introduction of the catheter and guidewire may occur in either order or at the same time. The distal tips of the guidewire 32 and the catheter 26 engage one another in the right atrium (56).

Next, the catheter is advanced to pull the guidewire 32 into coronary sinus 50 (58). The placement of the guidewire in coronary sinus 50 permits introduction of a sheath over the guidewire (60) to cannulate coronary sinus 50. The sheath advances over the guidewire into coronary sinus 50 (60). Once the sheath is advanced over the guidewire and into the coronary sinus, the guidewire and is disengaged from the steerable catheter (62).

Once the engagement is terminated, the catheter is withdrawn from the right atrium (64). In addition, the guidewire is withdrawn from the right atrium (66). The catheter and guidewire may be withdrawn in either order. After the guidewire is withdrawn, the cardiac lead may be advance into the sheath (68). Ultimately, sheath 38 is withdrawn (70), leaving the cardiac lead 40 positioned with the coronary sinus and, more particularly, the great vein proximate the left ventricle.

Figure 16:
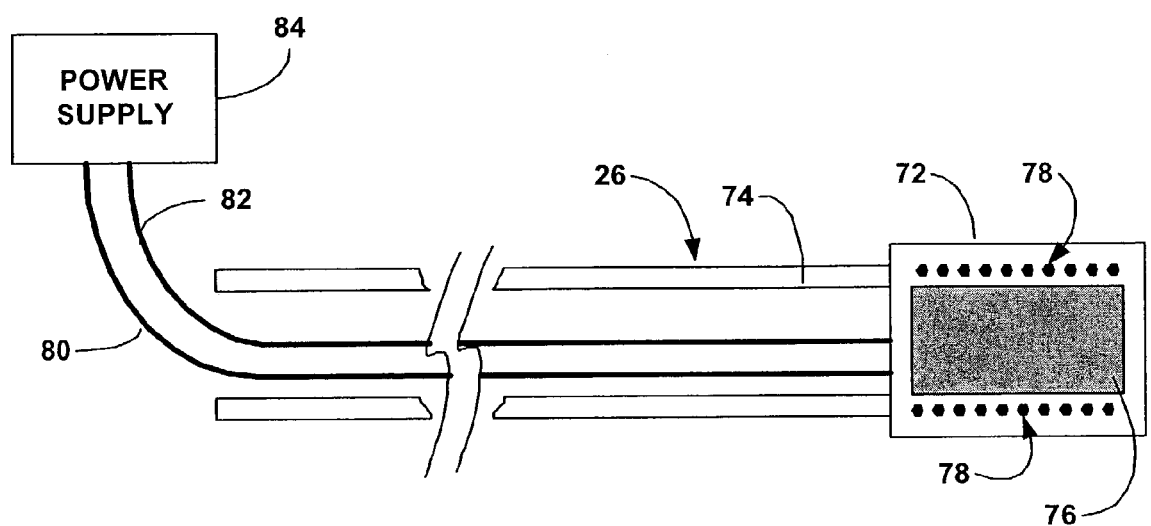
FIG. 16 is a cross-sectional side view illustrating a steerable catheter carrying an electromagnet assembly for use in coronary sinus cannulation.

FIG. 16 is a cross-sectional side view illustrating a steerable catheter 26 carrying an electromagnet assembly 72 for use in coronary sinus cannulation. Electromagnetic assembly 72 may be used as magnet 30 in some embodiments. As shown in FIG. 16, steerable catheter 26 defines an outer wall 74, and an electromagnet assembly 72 mounted at a distal tip of the catheter. Electromagnet assembly 72 includes a ferromagnetic core 76 and a winding 78 formed about the core. Ferromagnetic core 76 and winding 78 may be potted in a dielectric material. In addition, electromagnetic assembly may be mounted to the distal end of catheter 26 in a variety of ways, including adhesive bonding, ultrasonic welding, crimping and the like.

Winding 78 may be formed from multiple windings of electrical conductors 80, 82 about core 76. Conductors 80, 82 are coupled to terminals associated with a power supply 84. In operation, a surgeon guides steerable catheter 26 to a position within the right atrium, as described above, and activates power supply 84 to energize electromagnet assembly 72, e.g., with dc current, for engagement with a permanent magnet, electromagnet, or magnetically attractive metal carried by guidewire 32. When withdrawal of steerable catheter 26 is desired, the surgeon deactivates power supply 84 to deenergize electromagnet assembly 72, and thereby disengage the electromagnet assembly from the distal tip of guidewire 32.

A structure similar to that shown in FIG. 16 may be used to form an electromagnet for use as magnet 36 of guidewire 32. In that case, however, an insulating inner cover can be provided to insulate the electrical conductors from guidewire 32, in the event the guidewire is constructed from an electrically conductive material. Hence, an electromagnet may be provided on steerable catheter 26 to form magnet 30, on guidewire 32 to form magnet 36, or on both.

The invention may result in shorter coronary sinus cannulation time, and thus shorter surgery time. The invention may reduce the probability of an infection, reduce the probability of damage due to trauma from perforation or dissection during surgery, and help to prevent misplacement of the cardiac lead.

Various embodiments of the invention have been described. However, one skilled in the art will appreciate that various modifications may be made to these embodiments without departing from the scope of the invention. These and other embodiments are within the scope of the following claims. These and other embodiments are within the scope of the following claims.

What is claimed is:

1. A method of positioning an implantable medical device lead within a patient, comprising:

introducing a distal tip of a first elongated member along a first location within the patient through a first vein;

introducing a distal tip of a second elongated member within the first location through a second vein different from the first vein;

fixedly engaging the distal tip of the first elongated member with the distal tip of the second elongated member;

advancing the distal tip of the second elongated member to a second location, wherein the distal tip of the first elongated member is advanced to the second location with the distal tip of the second elongated member;

advancing an introducer sheath over the second elongated member and to the second location;

withdrawing the second elongated member from the first location; and introducing a cardiac lead to the second location via the introducer sheath, wherein the cardiac lead includes an electrical stimulation electrode, the method further comprising positioning the electrode in electrical contact with a third location via the second location, and wherein the first location corresponds to the right atrium, the second location corresponds to the coronary sinus, and the third location corresponds to the left ventricle.

2. The method of claim 1, further comprising withdrawing the first elongated member from the first location.

3. The method of claim 1, wherein the first elongated member includes a catheter.

4. The method of claim 1, wherein the second elongated member includes a guidewire.

5. The method of claim 4, wherein the distal tip of at least one of the first and second elongated members includes a magnet to fixedly engage the distal tip of the first elongated member with the distal tip of the second elongated member.

6. The method of claim 5, wherein the magnet is an electromagnet, the method further comprising energizing the electromagnet to fixedly engage the distal tip of the first elongated member with the distal tip of the second elongated member.

7. The method of claim 6, further comprising deenergizing the electromagnet to terminate the fixed engagement of the distal tip of the first elongated member with the distal tip of the second elongated member.

8. The method of claim 1, wherein engaging the distal up of the first elongated member with the distal tip of The second elongated member comprises magnetically engaging the distal tips.

9. A method of positioning an implantable medical device lead within a patient, comprising:
   introducing a distal tip of a first elongated member along a first location within the patient through a first introducing path;
   introducing a distal tip of a second elongated member within the first location through a second introducing path;
   engaging the distal tip of the first elongated member with the distal tip of the second elongated member;
   advancing the distal up of the, second elongated member to a second location, wherein the distal tip of the first elongated member is advanced to the second location with the distal tip of the second elongated member
   advancing an introducer sheath over the second elongated member and to the second location;
   withdrawing the second elongated member from the first location;
   introducing a cardiac lead to the second location via the introducer sheath; and
   advancing the sheath to disengage the distal tips of the first and second elongated members.

10. A method of positioning an implantable medical device lead within a patient, comprising:
    introducing a distal tip of a first elongated member along a first location within the patient through a first introducing path;
    introducing a distal tip of a second elongated member within the first location through a second introducing path;
    engaging the distal tip of the first elongated member with the distal up of the second elongated member; and
    advancing the distal tip of the second elongated member to a second location, wherein the distal tip of the first elongated member is advanced to the second location with the distal tip of the second elongated member, and wherein the first location corresponds to the right atrium, the first introducing path corresponds to the inferior vena cava, the second introducing path corresponds to the superior vena cava, and the second location corresponds to the coronary sinus.

* * * * *

UNITED STATES PATENT AND TRADEMARK OFFICE
CERTIFICATE OF CORRECTION

| | | |
|---|---|---|
| PATENT NO. | : 6,985,776 B2 | Page 1 of 1 |
| APPLICATION NO. | : 10/423113 | |
| DATED | : January 10, 2006 | |
| INVENTOR(S) | : Michael R. Kane et al. | |

It is certified that error appears in the above-identified patent and that said Letters Patent is hereby corrected as shown below:

Column 9, line 18, please delete "the distal up" and insert --the distal tip--

Column 10, line 22, please delete "the distal up" and insert --the distal tip--

Signed and Sealed this

Twenty-sixth Day of December, 2006

JON W. DUDAS
*Director of the United States Patent and Trademark Office*